United States Patent
Chauvel, Jr. et al.

(10) Patent No.: US 8,426,531 B2
(45) Date of Patent: Apr. 23, 2013

(54) METHOD FOR MONITORING MONOMER CONCENTRATION IN INTERFACIAL POLYCARBONATE MANUFACTURING PROCESS

(75) Inventors: Jean P. Chauvel, Jr., Lake Jackson, TX (US); John O. Osby, Lake Jackson, TX (US); Wenzel P. Bartlett, Clute, TX (US); Serena K. Stephenson, Lake Jackson, TX (US); John S. Hanson, Angleton, TX (US); Jeffery S. Bradley, Missouri City, TX (US); Walter D. Leatherwood, Lake Jackson, TX (US); Rajesh P. Paradkar, Lake Jackson, TX (US); Thoi H. Ho, Lake Jackson, TX (US)

(73) Assignee: Styron Europe GmbH, Horgen (CH)

( * ) Notice: Subject to any disclaimer, the term of this patent is extended or adjusted under 35 U.S.C. 154(b) by 0 days.

(21) Appl. No.: 13/254,062

(22) PCT Filed: Feb. 24, 2010

(86) PCT No.: PCT/US2010/025197
§ 371 (c)(1),
(2), (4) Date: Nov. 7, 2011

(87) PCT Pub. No.: WO2010/110984
PCT Pub. Date: Sep. 30, 2010

(65) Prior Publication Data
US 2012/0041158 A1    Feb. 16, 2012

Related U.S. Application Data

(60) Provisional application No. 61/162,701, filed on Mar. 24, 2009.

(51) Int. Cl.
| | | |
|---|---|---|
| C08F 283/00 | (2006.01) | |
| C08F 2/00 | (2006.01) | |
| C08L 69/00 | (2006.01) | |

(52) U.S. Cl.
USPC .............. 525/461; 525/469; 525/470; 526/60

(58) Field of Classification Search .................... 526/60; 525/461, 469, 470
See application file for complete search history.

(56) References Cited

U.S. PATENT DOCUMENTS
5,359,117 A    10/1994    Totani et al.

FOREIGN PATENT DOCUMENTS
| DE | 10 2005 01789 | 10/2006 |
|---|---|---|
| EP | 0 306 838 | 3/1989 |
| WO | WO 01/83583 | 11/2001 |
| WO | WO 01/83583 A1 * | 11/2001 |

\* cited by examiner

Primary Examiner — William Cheung
(74) Attorney, Agent, or Firm — Brinks, Hofer, Gilson & Lione (57) ABSTRACT

The present invention relates to an improved process for online measurement of monomer concentration, specifically bisphenol A, in an interfacial polycarbonate manufacturing process. Wherein the measurement is obtained by vibrational spectroscopy for the purpose of improving process control, specifically, controlling the carbonate polymer molecular weight.

10 Claims, 2 Drawing Sheets

FIG. 4

METHOD FOR MONITORING MONOMER CONCENTRATION IN INTERFACIAL POLYCARBONATE MANUFACTURING PROCESS

CROSS REFERENCE STATEMENT

This application is a U.S. National Stage of PCT/US10/25197 filed Feb. 24, 2010, which claims the benefit of U.S. Provisional Application No. 61/162,701, filed Mar. 24, 2009. The entire content of which is incorporated herein by reference.

FIELD OF THE INVENTION

The present invention relates to an improved process for online measurement of monomer concentration, specifically bisphenol A, in an interfacial polycarbonate manufacturing process. Wherein the measurement is obtained by vibrational spectroscopy for the purpose of improving process control, specifically, but not limited to, controlling the carbonate polymer molecular weight.

BACKGROUND OF THE INVENTION

In the practice of interfacial polymerization to produce polycarbonate, a mixture of dihydric phenol and a phenolic chain terminator is phosgenated under interfacial reaction conditions in the presence of an organic solvent. The dihydric phenol is present as an alkali metal salt in an aqueous phase and the phosgene is dissolved in the organic phase. The chain growing reaction is strongly accelerated by a coupling catalyst, such as a tertiary amine. Molecular weight of the polycarbonate polymer is typically controlled by the amount of chain terminator, such as a monophenol, present in the reaction mixture. The chain growing reaction is finished after all of the reactive end-groups, e.g., chloroformate end-groups, have reacted. After the polymerization step is completed, the organic phase comprising the polycarbonate polymer is separated from the aqueous phase and the polycarbonate polymer isolated.

Polymer molecular weight is one of the most important factors that affect polycarbonate polymer properties. As the polymer molecular weight increases, the mechanical properties of the polycarbonate polymer improve. For example, tensile strength, impact resistance, ductility, and other physical properties of the polymer are all improved with increasing polymer molecular weight. However, as the polymer molecular weight increases, the melt viscosity also significantly increases. When the melt viscosity becomes too high, melt processing the polymer becomes difficult or nearly impossible.

Ensuring consistent polycarbonate polymer quality in its manufacturing process is highly desirable. For example, if the polycarbonate polymer molecular weight and/or its molecular weight distribution falls outside a desired and/or targeted range, unacceptable amounts of unusable (sometimes referred to as out of spec or off-grade) polycarbonate may be produced. Minimizing the amount of off-grade polycarbonate provides many benefits to the manufacturer as well as the end user, to name a few, a better product, a more cost effective process, less waste, lower energy consumption and the like.

The molecular weight of a polycarbonate polymer produced in an interfacial process is dependent upon, among other things, the amount of dihydric phenol available for phosgenation and the amount of chain terminator. It has been found that in an interfacial polymerization process for manufacturing polycarbonate polymer the optimal pH is between 8.0 to 10.2, see U.S. Pat. No. 5,380,814. Further, it was determined under such conditions, not all the dihydroxy compound is available for reaction with phosgene. There is some dihydric phenol (which is not present as the bisphenate salt) which is soluble in water. Moreover, varying amounts of the dihydric phenol remain in the solid state, for example, because of inadequate agitation and/or because such solid dihydric phenol may attach itself to the upper portion of the reactor and remain unreacted. The amount that remains solid is neither consistent nor predictable. As a result, the amount of dihydric phenol (and therefore the resulting dihydric phenol to terminator ratio) which is fed to the reactor from its feed tank differs from the amount of dihydric phenol actually delivered through the process stream (resulting in the actual dihydric phenolate to terminator ratio which determines the molecular weight of the polycarbonate) into the polymerization reactor. The fluctuation in the ratio causes undesirable variations in the polycarbonate polymer molecular weight creating off-grade material with unacceptable properties and negative manufacturing cost ramifications.

Therefore, a method of reliably and quickly monitoring and controlling selected parameters which affect polycarbonate molecular weight in the interfacial process so as to ensure consistent product quality and high productivity would be very desirable.

SUMMARY OF THE INVENTION

The present invention provides such a method for online monitoring by using vibrational spectroscopy, preferably near infrared (NIR) spectroscopy, to determine concentrations of one or more reaction components, specifically dihydric phenolate and/or hydroxide concentrations, in an interfacial process to manufacture polycarbonate polymer. The determination of said concentrations is used to implement on-line, real time process control to feed rates of one or more reactants to control the polycarbonate polymer molecular weight.

According to the present invention, there is provided a method for controlling a dihydric phenolate to chain terminator ratio in an interfacial polycarbonate polymerization process by measuring the concentration of dihydric phenolate, preferably from bisphenol A, hydroxide, preferably from caustic, or both in an aqueous dihydric phenolate solution prior to reacting said solution with a carbonate precursor, preferably phosgene and a chain terminator, preferably phenol, para-cumyl phenol, or tertiary-butylphenol, in an interfacial polycarbonate polymerization process to produce a linear or a branched polycarbonate polymer, comprising the steps of:

i setting a target range for the dihydric phenol to chain terminator ratio;

ii introducing dihydric phenol and base at specific and independent feed rates into said solution;

iii setting target concentration ranges for dihydric phenolate and/or hydroxide in said solution;

iv introducing said solution, the carbonate precursor, and the chain terminator into a polymerization reactor at specific and independent feed rates;

v analyzing said solution, online prior to entering the polymerization reactor by vibrational spectroscopy, preferably using a Raman spectrometer, a mid infrared spectrometer, or a near infrared spectrometer, measuring the absorbance or scattering intensity of at least one wavelength as a reference wherein said solution has little to no absorbance, at least one wavelength wherein the dihydric phenolate absorbs, at least one wavelength wherein hydroxide absorbs, and at least one wavelength for temperature compensation;

vi calculating the concentration of the dihydric phenolate and/or hydroxide in said solution based on the vibrational spectrometer analysis;

vii comparing the calculated concentrations to the target concentration ranges; and viii using process control, when necessary, to adjust the feed rates of one or more of the dihydric phenol, the base, the chain terminator, and/or the dihydric phenolate solution to maintain the dihydric phenolate to chain terminator target range.

In on embodiment, the abovementioned method wherein the feed rate for the dihydric phenol and the feed rate for the base are kept constant and (1) the feed rate of the dihydric phenolate solution is held constant and the feed rate for the chain terminator is controlled, (2) the feed rate for the chain terminator is held constant and the feed rate for the dihydric phenolate solution is controlled, or (3) both the feed rates of the dihydric phenolate solution and the chain terminator are controlled to maintain the dihydric phenolate to chain terminator target range.

In another embodiment of the abovementioned method the polycarbonate polymer has a melt flow rate as determined at 300° C. and a load of 1.2 kilograms of from about 1 to about 100 grams per 10 minutes.

In yet another embodiment of the abovementioned method the online vibrational spectroscopic analysis is a near infrared analysis preformed by a single transmission cell, single light source, multi-filter photometer capable of measuring absorbance continuously and alternatively from 2 up to and including 8 different wavelengths.

In a preferred embodiment of the abovementioned method, the reference wavelength range is 7633 to 7752 $cm^{-1}$, the dihydric phenolate wavelength range is 5908 to 5997 $cm^{-1}$, the hydroxide wavelength range is 5642 to 5723 $cm^{-1}$, and the temperature compensation wavelength range 5457 to 5533 $cm^{-1}$.

In yet another embodiment the abovementioned method further comprises the step of maintaining the temperature of the dihydric phenolate solution during the analysis within a temperature range of about 55° C. to 65° C.

DETAILED DESCRIPTION OF THE INVENTION

Figure 1:
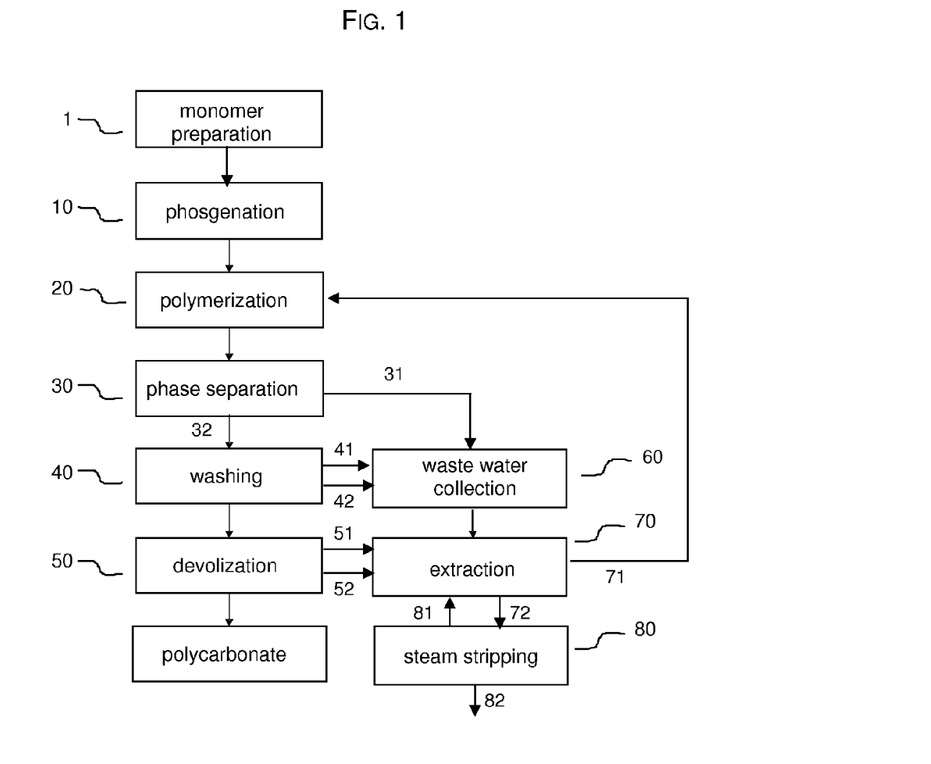
FIG. 1 is a flow chart of a conventional interfacial process for producing polycarbonate polymer.

FIG. 1 illustrates, in the form of a flowchart, a conventional interfacial polycarbonate manufacturing process in which the phosgenation reaction is conducted in step 10 followed by polymerization in step 20. In the phosgenation reaction 10, a carbonate precursor, preferably phosgene, dissolved in the water immiscible organic liquid is reacted with a salt of a dihydric phenol, commonly bisodium bisphenol A, to form carbonate oligomers having reactive chloroformate end-groups. The organic liquid is typically a chlorinated hydrocarbon such as dichloromethane although other organic liquids such as ethers, esters or ketones can be employed. The phosgene is normally employed in stoichiometric excess, typically 10 to 40 percent excess, in relation to the dihydric phenol. During phosgenation, the aqueous phase of the two phase reaction mixture is generally maintained at an alkaline pH, preferably from 9 to 14, by the addition of a base such as sodium hydroxide. The aqueous phase contains a dihydric phenol material, commonly a dihydric phenolate salt such as a salt of bisphenol A, for example, sodium bisphenolate. The dihydric phenolate is dissolved in an amount from 10 to 25 weight percent based on the total weight of aqueous solution.

The aqueous phase will also typically contain a chain terminator such as a sodium salt of a monofunctional phenolic compound, for example, phenol or 4-tert-butylphenol, and optionally a branching agent such as the sodium salt of a multifunctional phenolic compound. The chain terminator and optional branching agent may be added before or coincident with the coupling catalyst.

During the phosgenation reaction, salts such as sodium chloride and sodium carbonate are formed and dissolve in the aqueous phase. The carbonate oligomers formed enter the organic phase.

Following the desired phosgenation, a coupling catalyst typically, an amine coupling catalyst for example a tertiary aliphatic amine such as triethylamine, tripropylamine, or tributylamine, is added to the reaction mixture. A cyclic tertiary amine, such as dimethyl pyridine, may also be used as the coupling catalyst. The reactive carbonate oligomers are polymerized in the presence of the coupling catalyst during polymerization step 20 to the desired molecular weight.

The molecular weight of a polycarbonate polymer can be determined by techniques such as light scattering, viscosity, osmometry and freezing-point depression (unless noted otherwise, the term light scattering refers to steady state light scattering, as distinguished from dynamic light scattering). Viscosity can be used to determine the polymer molecular weight of solutions of polymers. For a dispersed two-phase mixture such as an interfacial process polycarbonate reaction mixture, the solution viscosity is also dependent on the water/organic solvent ratio, the temperature, and the reactor agitation rate, which introduces inaccuracies into this method. Unless otherwise noted, herein molecular weight refers to weight average molecular weight and is determined by gel permeation chromatography (GPC) using a bisphenol A polycarbonate standard and using standard molecular weight calculations, including the dispersity index.

Referring once again to FIG. 1, following the desired completion of the phosgenation reaction, the aqueous phase and the organic phase are separated in step 30. Techniques that effectively separate the two phases are well known and can be employed in the practice of this invention. The specific conditions and techniques used for this separation are not critical to the practice of this invention and any of the described can be employed. The separation is normally and preferably conducted using centrifugation.

In the process depicted in FIG. 1, the separated aqueous phase 31 (for purposes of describing this process, this will be referred to as wastewater) is fed to a waste water collection step 60. The wastewater contains salts made during the phosgenation reaction, typically NaCl and $Na_2CO_3$ but also contains traces of the organic liquid, reaction medium as well as dihydric phenol and/or other phenolic compounds.

The separated organic phase 32 will contain the organic reaction solvent, polycarbonate polymer as well as the coupling catalyst and dihydric phenolate salt, typically sodium dihydric phenolate. The coupling catalyst is generally in amounts of from 0.05 to 1 weight percent based on the total weight of the separated organic phase. The residual amounts of the dihydric phenolate salt (for example, sodium bisphenolate) are generally less than 0.1 weight percent.

The separated organic phase is washed in step 40. Techniques to wash the organic phase are well known in the art, not critical to the practice of this invention, and reference is made thereto for the purposes of this invention. Typically, the organic phase is washed with a dilute acid (for example, from 0.5 to 30 weight percent hydrochloric or phosphoric acid solution) to extract the amine coupling catalyst; followed by one to five wash steps with pure water. These water washes are generally performed in a sequence of conventional mixer-settler systems separators such as rotary mixers and liquid-liquid centrifuges or centrifugal extractors.

In the conventional method depicted in FIG. 1, the acidic wash water 41 and wash water(s) 42 are fed to the waste water collection step 60. The water wash(es) 42 following washing, contain phenolic compound, the coupling catalyst and, typically, traces of organic liquid, water soluble polycarbonate oligomers and dispersed polycarbonate particles. In the extraction step 70, the aqueous mixture solution comprising the wastewater, and/or acidic wash water, and/or water wash (es) are treated with caustic or other suitable basic material to adjust the aqueous mixture solution to an alkaline aqueous mixture solution having a pH of 12 or higher and free the amine. Conventional extraction techniques well known in the art can be employed in the practice of this invention. The specific conditions and techniques used for this extraction are not critical to the practice of this invention and any of the described can be employed. The extraction is normally and preferably conducted using extraction columns or centrifugal extraction.

In the extraction step 70, the phenolic materials, and any water soluble oligomers, and dispersed polycarbonate particles are removed from the wash water and wastewater by extraction with the organic liquid containing the amine coupling catalyst. Conveniently, for ease of further processing the organic liquid used to the treat the wash water and/or wastewater is the organic liquid used in the organic reaction phase 10 as well as the organic reaction phase 52 removed in the devolatization step 50. The organic liquid, coupling catalyst and extracted or removed phenolic materials may be recycled 71 to the reaction mixture polymerization step 20 as shown in FIG. 1. It is desirable to recycle 71 directly back into 20 as amine coupling catalysts may react with chlorinated hydrocarbon solvents such as dichloromethane to form undesirable quaternary ammonium salts if the residence time in the recycle system and/or storage time is too long. The treated water, which contains organic liquid as well as traces of the coupling catalyst, is fed 72 to steam stripping step 80.

Steam stripping is a technique well known in the art and reference is made thereto for the purposes of this invention. It is conducted at conditions to remove the remaining organic liquid and coupling catalyst in the form of vapor from the aqueous liquid. Typically, the steam stripping operation is conducted by exposing the aqueous liquid to steam at a temperature of from 100 to 200° C. The organic liquid and coupling catalyst vaporized in the steam stripping operation are then condensed 81 and recycled from the treated wash and wastewater back to the extraction step 70. Alternatively, the removed organic liquid and coupling catalyst 81 can be recycled, in whole or in part, directly to the reaction mixture, preferably the polymerization reaction 20.

Following steam stripping, the aqueous phase 82, is disposed. Provided concentration of phenolic components, water soluble oligomers, dispersed polycarbonate particles is sufficiently small, the aqueous phase can be released to a salt containing environment such as the sea or brackish water or brine wells without further treatment. Alternatively, the aqueous liquid can be used in other operations such as chlor-alkali electrolysis.

Following washing, the polycarbonate is isolated from the organic phase in a recovery step 50 using techniques well known in the art such as devolitization (that is, steam evaporation of the solvent, or evaporation of the solvent in an extruder), or precipitation with a nonsolvent for the polycarbonate such as hexane or like means. Water 51 from step 50, which is generally saturated with the organic liquid reaction medium, is preferably fed back to different points of the process such as the wash section 40 or alternatively, the steam stripper 80 or, as depicted in the FIG. 1, the extraction step 70.

Figure 2:
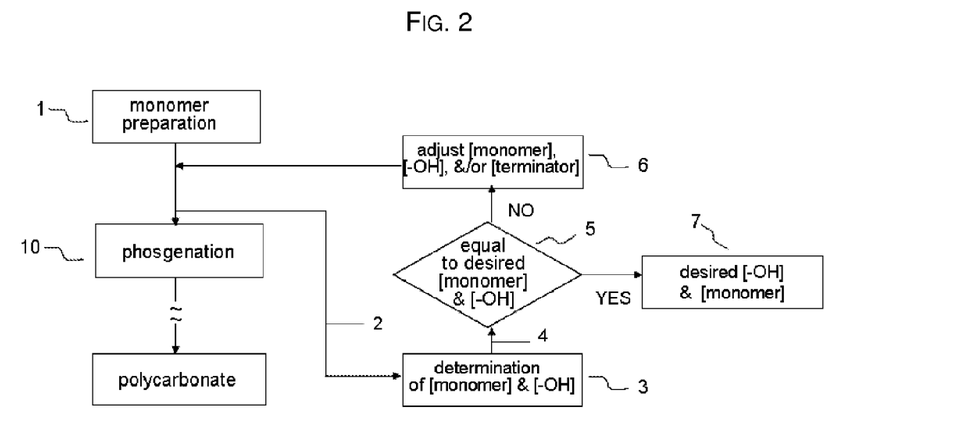
FIG. 2 is a flow chart for one embodiment of an interfacial process for producing polycarbonate polymer comprising the online monitoring system of the present invention.
Figure 3:
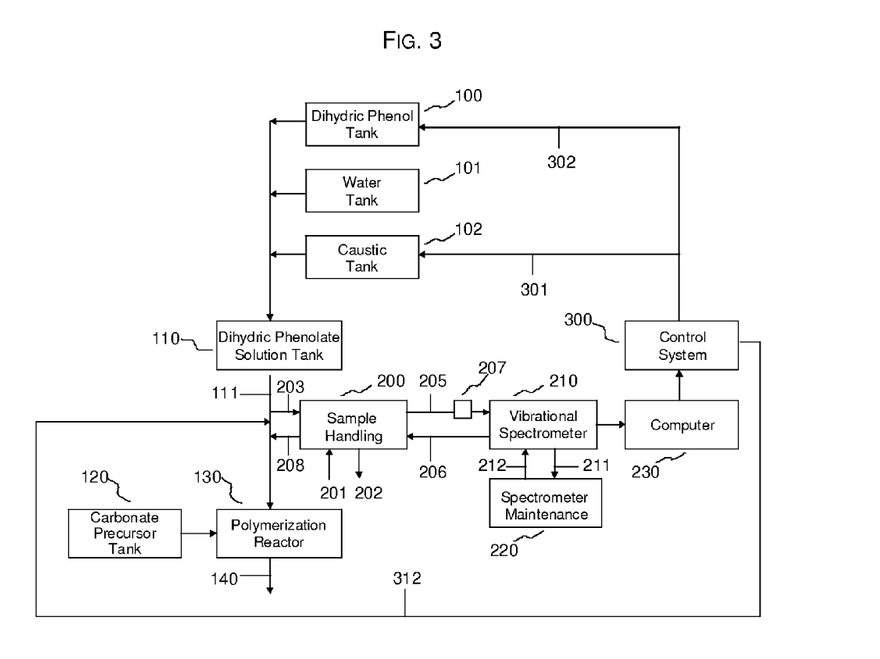
FIG. 3 is a schematic diagram of one embodiment of the online monitoring system of the present invention for an interfacial process for producing polycarbonate polymer.

An embodiment of the process of the present invention is shown as a flow chart in FIG. 2 and as a process schematic in FIG. 3. The improvement of the process of the present invention over conventional interfacial polycarbonate manufacturing processes is the ability to improve molecular weight control by maintaining a target dihydric phenol monomer (measured as the dihydric phenolate) to chain terminator ratio. This is accomplished by real time process control adjustments of one or more of the dihydric phenol flow rate into the dihydric phenolate solution tank, the base into the solution tank, the feed rate of the dihydric phenolate solution into the polymerization reactor, and/or the feed rate of the terminator into the polymerization reactor. A preferred method is to adjust the feed rate of the dihydric phenolate solution to the polymerization reactor while keeping the feed rate of the chain terminator constant.

The specific dihydric phenol to chain terminator ratio depends on the desired polycarbonate polymer molecular weight and can easily be determined by one skilled in the art. The acceptable range for the ratio is sometimes referred to as the molecular weight specification; polycarbonate polymer falling within the range meets the specification and is acceptable. Polycarbonate polymer falling outside of the range is out of specification and is unacceptable, this is sometimes referred to as out of spec material or off-grade.

The dihydric phenol, water, and caustic are fed from feed tanks 100, 101, and 102, respectively into a solution tank 110 at independent, determined and controllable feed rates. The feed rates are each set to meet target ranges for the dihydric phenolate and hydroxide concentration. These target concentration ranges in combination with a calculated amount of chain terminator are set to produce a polycarbonate polymer having a molecular weight within a desired range, or specification. The concentration of the dihydric phenolate, preferably the sodium salt of bisphenol A, and/or the concentration of the hydroxide in the aqueous dihydric phenolate mixture process stream 111 are determined between the solution tank 110 and the polymerization reactor 130 or, in other words, after the monomer preparation step 1 and before the phosgenation step 10. The determination 3 is done via an online vibrational spectrometer, preferably a Raman spectrometer, an infrared, a mid infrared spectrometer, or a near infrared spectrometer 210 wherein the concentration of the dihydric phenolate and/or hydroxide are determined by spectral readings, specifically absorbance or scattering intensity at one or more specific wavelength. The vibrational absorbance (or scattering intensity) is converted using standard and readily available software to a concentration level by a computer 230. The computer 230 relays its signals to the control system 300, the levels of dihydric phenolate and/or hydroxide are determined to be acceptable or not 5, and real time changes 6 or 7 to one or more of the feed rate(s) of dihydric phenol and/or caustic into the dihydric phenolate solution tank 110 are made as desired. Alternatively, the feed rate of the dihydric phenolate solution into the polymerization reactor 130 may be adjusted, preferably while keeping the feed rate of the chain terminator to the polymerization reactor constant. Alternatively, the feed rate of the chain terminator (not shown in the FIGs.) into the polymerization reactor 130 may be adjusted, preferably while keeping the feed rate of the dihydric phenolate solution to the polymerization reactor constant.

In one embodiment of the present invention the sample line 203 from the aqueous dihydric phenolate mixture process stream 111 enters the vibrational spectrometer 210 directly and loops directly back through a return line 208 to the aqueous dihydric phenolate mixture process stream 111. In one embodiment of the present invention, the sample handling system 200 may contain valves (not shown in FIG. 3) to shut off the flow of aqueous dihydric phenolate mixture allowing flushing and/or zeroing of the analyzer 210. In yet another embodiment of the present invention, in order to control the flow of the sample, the sample handling system 200 may have means to increase or decrease the pressure of the aqueous dihydric phenolate mixture in the sample line 205 entering the analyzer as compared to the pressure in the process line 111 between the dihydric phenolate solution tank 110 and the polymerization reactor 130. In yet another embodiment of the present invention, the sample handling system 200 may dilute the aqueous dihydric phenolate mixture, for example by adding water to the sample, prior to entering the sample line 205 to the analyzer 210. In yet another embodiment of the present invention, the sample handling system 200 may comprise means to take 'grab samples' of the dihydric phenolate mixture process sample to be analyzed off-line. In yet another embodiment of the present invention, the sample handling system 200 has a fast loop means off the sample line enabling analysis of smaller quantities of sample and resulting in faster response time. In yet another embodiment of the present invention, the sample handling system 200 has one or more filters to decrease plugging and fouling of the sample lines. In a preferred embodiment of the present invention, the aqueous dihydric phenolate mixture sample 500 passes through a sample handling system 200 which may comprise a heating means for controlling the temperature of the sample of aqueous dihydric phenolate mixture to be analyzed. The sample lines from and/or returning to the aqueous dihydric phenolate mixture process stream to the sample handling system 200 and/or the vibrational spectrometer 210 may or may not be temperature controlled (e.g., heated or cooled) as desired. The sensor for temperature control of the aqueous dihydric phenolate mixture sample line 207 is in direct contact with the sample immediately before the vibrational spectrometer 210.

If the sample lines are temperature controlled, the temperature is determined by the desired species is to be monitored, the specific dihydric phenol, the preferred wavelength, and the like. A preferred target temperature is selected within a range from about 40° C. to about 80° C., more preferably about 40° C. to about 70° C., more preferably from about 50° C. to about 70° C., and more preferably from about 55° C. to about 65° C. Preferably the temperature is controlled to within about +/−10° C. of the desired temperature target, more preferably about +/−5° C. of the desired temperature target.

Depending on the vibrational spectrometer employed in the process of the present invention, there may be a spectrometer maintenance system 220 which allows for specific requirements of the spectrometer 210. For example, the spectrometer maintenance system 220 may be used for one or more of the following: purging and/or cleaning the sample cell(s) or probe(s), providing a means to introduce air or an inert (or other type of) gas into the analyzer as required for its routine operational needs, for instance to purge the optics and/or electronics, providing a means to temperature control the analyzer and/or its sample, providing a means for introducing a zero sample and a span sample for routine calibration checks, providing a means to collect a process sample for laboratory comparison (sometimes called a grab sample), and the like.

The polycarbonate production (both phosgenation and polymerization) can be carried out in a batchwise or continuous fashion. Batchwise production is conducted in a stirred tank whereas the more preferred continuous technique typically makes use of a series of stirred tanks or one or more tubular reactors. In general, phosgenation and polymerization are conducted in the same reactor vessel or without any intermediate purification or other steps between the phosgenation or polymerization reaction.

The dihydric phenols employed in the practice of the present invention are generally known in the carbonate polymerization art and in which the only reactive groups under condensation polymerization conditions are the two phenolic hydroxyl groups. Useful dihydric phenols are for example those of the general formula HO—Z—OH, wherein Z comprises a mono- or poly-aromatic diradical of 6-30 carbon atoms, to which the phenolic oxygen atoms are directly linked. The aromatic group(s) may comprise one or more heteroatoms and may be substituted with one or more groups, for example one or more oxygen, nitrogen, sulfur, phosphorous and/or halogen, one or more monovalent hydrocarbon radical, such as one or more alkyl, cycloalkyl or aryl groups and/or one or more alkoxy and/or aryloxy groups. Preferably, both phenolic hydroxy groups in the dihydric phenol HO—Z—OH are arranged in para-positions on the aromatic ring(s).

The dihydric phenols employed in the process of the present invention include the bis(aryl-hydroxy-phenyl)alkylidenes including their aromatically and aliphatically substituted derivatives, such as disclosed in U.S. Pat. No. 2,999, 835; U.S. Pat. No. 3,038,365; U.S. Pat. No. 3,334,154 and U.S. Pat. No. 4,299,928; and aromatic diols such as described in U.S. Pat. No. 3,169,121.

Preferred examples of dihydric phenols of the general formula HO—Z—OH are bis(hydroxyphenyl)fluorenes, such as 9,9-bis-(4-hydroxyphenyl)fluorene; dihydroxy benzenes and the halo- and alkyl-substituted dihydroxy benzenes, such as hydroquinone, resorcinol, or 1,4-dihydroxy-2-chlorobenzene; alpha,alpha'-bis(hydroxyphenyl)-diisopropylbenzenes; dihydroxybiphenylenes, such as 4,4'-dihydroxydiphenyl; the halo- and alkyl substituted dihydroxybiphenylenes; bis(hydroxyphenyl)alkanes, such as bis(4-hydroxylphenyl) methane, 1,1-bis(4-hydroxyphenyl)ethane, 1,1-bis(4-hydroxyphenyl)propane, or, most preferably, 2,2-bis(4-hydroxyphenyl)propane ("bisphenol A"); alkyl-, aryl- or halosubstituted bis(hydroxyphenyl)alkanes, such as 1-phenyl-1,1-bis(4-hydroxyphenyl)ethane ("bisphenol AP"), 2,2-bis(3,5-dibromo-4-hydroxyphenyl)propane ("tetrabromo bisphenol A"), 2,2-bis(3,5-dimethyl-4-hydroxyphenyl)propane ("tetramethyl bisphenol A"); optionally alkyl-, aryl- or halosubstituted bis(hydroxyphenyl)cycloalkanes; optionally alkyl-, aryl- or halosubstituted bis(hydroxyphenyl)ethers; optionally alkyl-, aryl- or halosubstituted bis(hydroxyaryl) sulfones, preferably bis(hydroxyphenyl)sulfones; or bis(hydroxyphenyl)sulfoxides. Other examples of suitable dihydric phenols are listed in U.S. Pat. No. 4,627,949, column 2, line 68-column 3, lines 1-22, in U.S. Pat. No. 4,962,144, column 2, lines 17-46 and in EP 423 562, page 2, lines 24-55 and page 3, lines 1-19. Mixtures of two or more dihydric phenols may also be used, for example a mixture comprising 1-99 percent of bisphenol A and 99-1 weight percent of another dihydric phenol, such as 9,9-bis-(4-hydroxyphenyl)fluorene.

Among the most preferred dihydric phenol suitable for production of polycarbonate in the present invention are bisphenol A, bisphenol AP, tetrabromo bisphenol A, and tetramethyl bisphenol A. The most preferred dihydric phenol is bisphenol A.

The aqueous alkaline solution has a pH range from equal to or greater than about 9.5, preferably equal to about 14, preferably equal to or greater than about 12 to less than or equal to about 14, and can be formed in water by adding base such as caustic soda, NaOH, or other bases such as alkali metal and alkaline earth metal carbonates, phosphates, bicarbonates, oxides and hydroxides. Base is typically used over the course of the interfacial polymerization and further added to the reaction mixture where appropriate to maintain the proper pH. In total this usually amounts to the addition of base in an amount of 2 to 4, preferably 3 to 4, moles base per mole of dihydric phenol compound. The base, such as caustic soda, is added to the reaction mixture to adjust the pH of the mixture to a level at which the dihydric phenol compound is at least partially converted to dianionic form. A reducing agent such as sodium sulfite or sodium dithionite can also be advantageously added to the reaction mixture as well. A preferred molar ratio of bisphenol A to hydroxide in the dihydric phenolate solution tank is 1.9 to 2.2, preferably 2.0 to 2.1

A carbonate precursor suitable for use in the present invention contains leaving groups which can be displaced from the carbonyl carbon in attack by the anion of a dihydric phenol compound, and includes but is not necessarily limited to carbonyl halides or acyl halides, of which, the most preferred is phosgene. The carbonate precursor, preferably phosgene, is contacted with the dihydric phenol compound in the aqueous alkaline solution and can be added as a solution in the water-immiscible non-reactive organic solvent and thoroughly mixed with the aqueous phase or can be bubbled into the reaction mixture in the form of a gas and preferentially dissolve and locate in the organic phase. The carbonate precursor is typically used in an amount of 1.0 to 1.8, preferably 1.1 to 1.4, moles per mole of dihydric phenol compound. Representative solvents include chlorinated hydrocarbons such as methylene chloride, 1,2-dichloroethane, tetrachloroethane, chlorobenzene, and chloroform, to which tetrahydrofuran, dioxane, nitrobenzene, dimethyl sulfoxide, xylene, cresol or anisole may be added, if desired.

Both phases are mixed in a manner which is sufficient to disperse or suspend droplets of the solvent containing the carbonate precursor in or otherwise contact the precursor with the aqueous alkaline mixture. Reaction between the carbonate precursor and the phenate reactant in the aqueous phases yields primarily the bis-ester of the carbonate precursor with the dihydric phenol compound which can further react with more dihydric phenol units to form longer chain oligomers. Oligomer is defined as a polycarbonate chain having 15 or less repeating units. Some dihydric phenol does not react in this phosgenation step and remains as a monomer but will react later with the chloroformate end-groups, formed in the phosgenation, and some remains as shorter chain, intermediate bis-esters. For example, if the carbonate precursor is an acyl halide such as phosgene, these intermediates are primarily bischloroformates, although some end groups may instead be a terminator residue, phenolate ion or unreacted hydroxy group.

A chain terminator is a monofunctional compound containing a functional group, frequently a hydroxyl group, which will produce an anion capable of displacing an unreacted chloroformate group which remains on the end of the oligomer or polymer chain. Representative of the terminators which are useful for the production of polycarbonates in the present invention are phenol and the derivatives thereof, saturated aliphatic alcohols, metallic sulfites, alkyl acid chlorides, trialkyl- or triarylsilanols, monohalosilanes, amino alcohols, trialkyl alcohols, aniline and methylaniline. Of these, phenol, para-t-butyl phenol (PTBP), p-cumyl phenol and para-t-octyl phenol(4-(1,1,2,2-tetramethylbutyl)-phenol or PTOP) are the most preferred for use in the present invention. The amount of chain terminator used is dependent on the desired molecular weight of the polycarbonate polymer and is easily determined by one skilled in the art, but typically the range is based on a ratio of bisphenol A to terminator of from about 1 to 10 to about 1 to 50.

Branching agents (typically phenols having three or more hydroxy or condensation reactive groups) can be employed to obtain branched polycarbonates with the desired molecular weight and branching degrees. Suitable branching agents are generally one or more of the following: phloroglucin; phloroglucid; 2,6-dimethyl-2,4,6-tri(4-hydroxyphenyl)heptene-3; 4,6-dimethyl-2,4,6-tri(4-hydroxyphenyl)heptene-2; 4,6-dimethyl-2,4,6-tri(4-hydroxyphenyl)pentene-2; 4,6-dimethyl-2,4,6-tri(4-hydroxyphenyl)pentane; 1,3,5-tri(4-hydroxyphenyl)benzene; 1,3,5-tri(2-hydroxyphenyl)benzol; 1,1,1-tri(4-hydroxyphenyl)ethane; 2,6-bis(2-hydroxy-5-methylbenzyl)-4-methylphenol; tetra(4-hydroxy-phenyl)methane; trisphenol; bis(2,4-dihydroxyphenyl)ketone; 1,4-bis(4,4-dihydroxytriphenylmethyl)benzene; $\alpha,\alpha',\alpha''$-tri(4-hydroxyphenyl)-1,3,5-tri-isopropylbenzene; 3,3-bis(4-hydroxyaryl)oxyindole; isatinbisphenol; 5-chloroisatin; 5,7-dichloroisatin; 5-bromoisatin; trimellitic acid; pyromellitic acid; benzophenonetetracarboxylic acid; and including for the appropriate compounds, the acid chlorides or other condensation reactive derivatives thereof such as trimellitic trichloride, trimesoylchloride and trimellitic anhydride chloride. Specifically preferred branching agents include phloroglucin; phloroglucid; 1,1,1-tri(4-hydroxyphenyl)ethane; trimellitic acid; trimellitic trichloride; pyromellitic acid; benzophenonetetracarboxylic acid and acid chlorides thereof; 2,6-bis(2-hydroxy-5-methylbenzyl)-4-methylphenol and 1,3,5-tri(4-hydroxyphenyl)benzene.

It has been found that levels of branching agent in the branched carbonate polymer components for use in the present invention should be in the range of from about 0.005 to about 1 mole branching agent per mole of dihydroxy compound, preferably from about 0.01 to about 0.8, and more preferably from about 0.1 to about 0.6.

Suitable coupling catalysts include a tertiary amine such as triethylamine (TEA), dimethyl amino pyridine or N,N-dimethyl aniline; a cyclic aza compound such as 2,2,6,6-tetramethyl piperidine or 1,2-dimethylimidazole; an iminoether or iminocarboxylate compound such as 1-aza-2-methoxy-1-cycloheptene or t-butyl-cyclohexyliminoacetate; or a phosphonium, sulfonium, arsonium or quaternary ammonium compound such as cetyl triethylammonium bromide. Tertiary amines are the preferred coupling catalysts for use in improved process according to the present invention and include trimethylamine, triethylamine, tributylamine, and 4-N,N-dimethylaminopyridine.

In this process, the coupling catalyst is generally used in amounts typically ranging from about 0.001 to about 0.1 moles per mole of dihydric phenol compound. The catalyst is preferably added in amounts of at least about 0.0025, preferably at least about 0.008 and more preferably at least about 0.015 moles per mole of dihydric phenol compound. The catalyst is preferably added in amounts up to about 0.15, preferably up to about 0.1 and more preferably up to about 0.075 moles per mole of dihydric phenol compound. Some or all of the catalyst is added at the beginning of the polymerization process. Optionally, the coupling catalyst addition is split with a second part added later in the polymerization process.

Polycarbonate polymers of the present invention have a melt flow rate (MFR) of from about 1 gram per 10 minutes (g/10 min) to about 100 g/10 min, preferably from about 2 g/10 min to about 90 g/10 min, more preferably from about 3 g/10 min to about 80 g/10 min. Unless otherwise noted, MFR are determined at determined under the conditions of 300° C. and a load of 1.2 kilograms Referring now to FIG. 3 and FIG. 4, the vibrational spectrometer (in FIG. 4 a NIR spectrometer is depicted) 210 collects absorption intensities at the filter wavelengths of the solution flowing through the sample cell 419 and to the integrated computer 230. Among other functions, the computer (1) performs calculations on the absorption intensities to compare determined values to targeted values of the concentration of dihydric phenate and/or the concentration of hydroxide and (2) based on these comparisons, sends control commands to the control system to enable real time process control. For example, for polycarbonate made from bisphenol A and caustic, the calculations utilize absorption intensities acquired for four filter wavelengths chosen between about 5400 reciprocal centimeters ($cm^{-1}$) and 7700 $cm^{-1}$. There is flexibility as to the exact number of filters and filter wavelengths chosen. In one embodiment, the region from 7633 to 7752 $cm^{-1}$ is selected for the reference, 5908 to 5997 $cm^{-1}$ is selected for the bisphenol A, 5642 to 5723 $cm^{-1}$ is selected for the NaOH, and 5457 to 5533 $cm^{-1}$ is selected for an temperature compensation.

Temperature compensation is preferably employed to compensate for change in spectral profile at varying temperatures. The integrated computer board takes the absorption intensities and applies the calibration matrix to predict the concentration. One of the wavelength regions acts as the baseline reading and is incorporated into the matrix calculation. This eliminates the spectral pretreatment (e.g. mean centering, smoothing, etc.) that is required when using a full-spectrum spectrometer. The computer outputs the predicted concentration(s) to the plant's control system via a typical I/O interface which are well known in the art. The control system, also well known in the art, then applies the appropriate logic to determine what actions should be taken based on the results.

There are several suppliers of suitable photometer technologies, such as the Optical Solutions line of Guided Wave (Rancho Cordova, Calif.), and ABB Inc. (Cary, N.C.). In addition to photometers other mid or near infrared vibrational spectroscopic techniques can be employed for the dihydric phenolate and hydroxide analysis. For example a full-spectrum analyzer based on a Michelson interferometer, a diode array spectrometer, and an EPIR disk spectrometer are all options. Some examples of suppliers are: Analect Hamilton Sundstrand (Pomona, Calif.); Guided Wave (Rancho Cordova, Calif.); NIRSystems (Silver Spring, Md.); Perkin Elmer (Norwalk, Conn.); Varian Associates (Sunnyvale, Calif.); Moisture Systems Corp. (Hopkinton, Mass.); Carl Zeiss MicroImaging GmbH (Germany); and LT Industries, Inc. (Rockville, Md.)). The equipment vendors normally supply, with their equipment, a comprehensive set of operating software, which permits the user to operate his or her vibrational spectrometer and to analyze the data. Some systems have an integrated computer and some have a computer attached externally. The computer is used for analyzer control and data interpretation.

In addition to vibrational spectroscopic techniques based on absorption, Raman spectroscopy is a scattering technique probing molecular vibrations and could also be employed for the dihydric phenolate and hydroxide analysis. Some examples of suppliers for process Raman systems are: Kaiser Optical Systems, Inc. (Ann Arbor, Mich.); Bruker (Billerica, Mass.); Analect Hamilton Sundstrand (Pomona, Calif.); and Process Instruments (Salt Lake City, Utah).

Dedicated process vibrational spectrometers or modified laboratory vibrational spectrometers of conventional design can be used with the invention. The preferred system here is a robust and relatively simple NIR photometer operated in a transmission mode using an extractive sample cell with a 1 millimeter (mm) pathlength. Other suitable modes of operation, depending on the spectrometer design are reflectance and transflectance with the option of either an extractive system or a process insertion probe. The spectrometer can be operated on a batch basis (receiving signals, e.g., by a sample feeding arrangement), or more preferably, on a continuous basis in which the fluid to be measured flows through a cell, or a probe is immersed in the flowing fluid, and light is transmitted through a fiber-optic cable to and from the spectrophotometer.

When a full-spectrum spectrophotometer is used to scan a process stream, a lengthy series of discrete results are collected at each wavelength step by the instrument. The resulting response at each wavelength is expressed in transmittance (T), reflectance (R), or absorbance (A) units, A being equal to log (1/T). When T=1, no absorbance occurs; while when T=0, infinite absorbance occurs. When these results are plotted vs. wavelength, a spectrum (curve) is produced. The field of chemometrics deals with the appropriate ways to treat this data mathematically, in conjunction with calibration and validation concentration data in order to extract meaningful information usually by using either a Complete Least Squares (CLS) or a Partial Least Squares (PLS) model.

In the case of a filter photometer this is simplified. Instead of having a lengthy series of discrete results, there is a filter absorbance each of the filters (e.g., for each wavelength measured). For example, if the photometer has 8 filters, there will be 8 absorbance values. During the initial photometer calibration, absorbances are collected for a series of known calibration samples with concentrations establish by independent means (i.e. a reference method). A simple regression, such as is available in Excel, is carried out on the filter absorbances to determine the matrix coefficients and the normalization coefficient (i.e. response factor) to be input into the analyzer for each component. These coefficients are entered into the photometer and the computer then applies them to all future data collection. Generally a set of validation samples are analyzed on the system to determine the standard error of prediction for the model.

There are many well-known mathematical techniques of correlation of vibrational spectral responses. They include, for example, "Single-Term Linear Regression," "Multiterm Linear Regression," "Component Spectrum Reconstruction," and "Discriminant Analysis" methods explained in an article by W. R. Hruschka at pp. 35-55 of Near Infrared Technology in the Agricultural and Food Industries, P. C. Williams et at., Editors, American Association of Cereal Chemists, Inc. St. Paul, Minn. 1987 ("Williams"). Other techniques include, for example "Hruschka Regression, "Fourier Transform Regression," "Principal Component Regression," and "Partial Least Squares Regression" methods explained in detail in an article by H. Martens et al., at pp. 57-87 of Williams. In Chapter 3 of Multivariate Calibration, H. Martens et at., John Wiley & Sons, Ltd., Chichester, U.K. 1989, more techniques, including, for example, "Univariate Calibration," "Bilinear Modeling," "Self Deconvolution," "Target Transformation Factor Analysis," "Rank Annihilation Method," "Step-wise Multiple Linear Regression," "Ridge Regression," "Nonlinear Regression," and "Nonparametric Regression" are taught. The "Neural Network" technique explained in D. E. Rumelhart et al. in Parallel Distributed Processing-Explorations in the Microconstruction of Cognition, Vol. 1, Foundations 1986; Vol. 2, Psychological and Biological Models, 1986; and Vol. 3, A Handbook of Models, Programs and Exercises, 1988, MIT Press Cambridge, Mass., may also be applied.

Some commercially available software packages include, for example, "Near infrared Spectral Analysis Software" (NSAS) by NIRSystems, Inc., Silver Spring, Md.; "Unscrambler" by Camo A/S, Trondheim, Norway; "Spectra Metrix," "LightCal," and "LightCal Plus" by LT Industries Corporation, Rockville, Md.; and "InfraAnalyzer Data Analysis System" (IDAS) and "Principal Component Analysis Program" (PCA-pc) by Bran+Luebbe Analyzing Technologies, Inc.

The results of measurement determinations are transmitted instantaneously to a process control system, whose role is to control the process variables such as, control the feed rate of the dihydric phenolate solution that is fed into the polymerization reactor. One embodiment of control is an automated distributive control system (DCS) comprising a process computer which is linked directly to the near infrared analyzer. The process control computer is provided with an algorithm by which it controls the process. Another embodiment of control comprises simple monitoring by an operator who makes appropriate manual adjustments to process variables.

Figure 4:
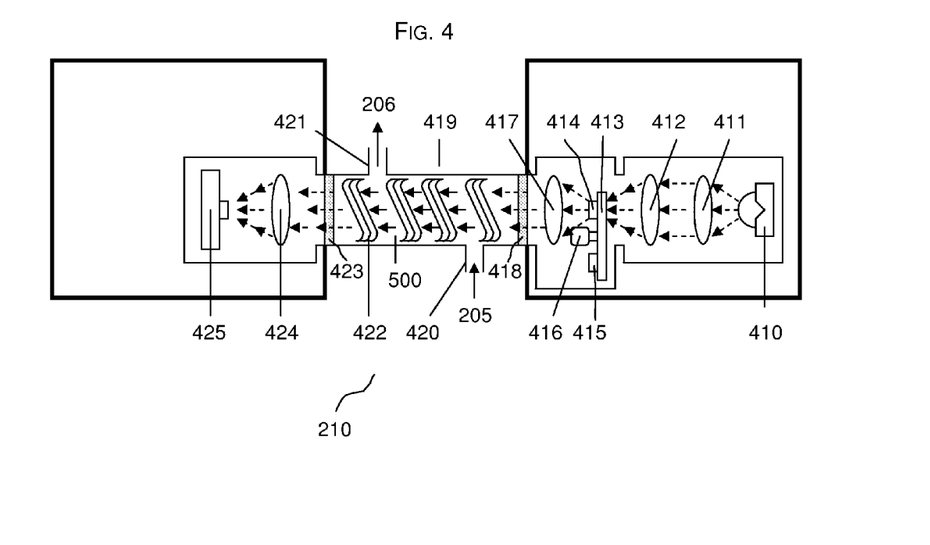
FIG. 4 is a schematic diagram of a single transmission cell, single light source, multi-filter NIR photometer.

A preferred NIR spectrometer 210 for use in the present invention comprises a single transmission cell, single light source, multi-filter photometer FIG. 4 capable of providing a ratio of the transmitted energy between a reference wavelength and measured wavelengths by measuring a reference wavelength where the aqueous dihydric phenolate mixture sample 500 has little or no absorbance and one or more wavelengths where the dihydric phenolate and/or hydroxide have absorbance. It also comprises a microprocessor (not shown in FIG. 4) capable of employing matrix algebra and applying the proper response factor to each wavelength determination to eliminate interference on the desired component and convert the absorbance to a component concentration. The light source 410 is preferably a Tungsten NIR lamp. A preferable analyze may have a collimating lens (L1) 411 through which the light from the light source passes. After the collimating lens (L1) 411 the light is refocused through an optical filter (L2) 412 on a 'filter wheel' (FW) 413. The filter wheel comprises one, two, three, four, five, six, seven, eight, or more filters 414 and 415, each selects a different wavelength (frequency range) of interest. For instance, filter 1 (F1) 414 is set as the background or reference filter and is set at a wavelength where the light of the aqueous dihydric phenolate mixture sample 500 is minimal. The filter wheel has a means, such as a brushless chopper motor 416, for rotating the filters 414 and 415 continuously and alternately in and out of the light path. After passing though a filter, the light consisting of only the desired frequency region covered by the filter is recollimated through a third lens (L3) 417 and directed through a first window 418 of the spectrometer sample cell 419. The aqueous dihydric phenolate mixture sample 500 flows into the sample cell 419 through an inlet 420 and out through an outlet 421. The spectrometer sample cell 419 is optionally contains a mixing means 422. The components in the aqueous dihydric phenolate mixture sample 500 that absorb in the wavelength of the specific lens (e.g., L1, L2, L3, L4, L5, L6, L7, L8, etc.) reduce the intensity of the light via a vibrational molecular absorption mechanism. After passing through the first window 418 into, through, and out the sample cell 419 through the second window 423, the light is focused through a lens (L4) 424 onto a detector (D) 425. The detector response is the absorbance of the sample for the given filter and is input into the matrix algebra used within the spectrometer computer to calculate the actual sample component concentrations, i.e., dihydric phenolate and/or hydroxide concentrations.

A suitable NIR spectrometer enables multicomponent analysis, a single optical path from the light source to the detector (in other words does not require the use of minors), has a simple mechanical design that allows for easier service and maintenance, can compensate for obstruction of cell windows (up to 50 percent obscured without affecting measurement accuracy), compensates for light source and detector aging, permits the sample cell to be isolated from the electronics, and/or has temperature control of the sample cell to minimize temperature fluctuations. An example of such a preferred NIR spectrometer is the Process Photometer PIR 3502 manufactured by ABB Inc.

In the process of the present invention, preferably the reference wavelength range (F1) is from 7633 to 7752 $cm^{-1}$. The wavelength for the dihydric phenolate depends upon the specific bisphenolate being monitored, for instance for the salt of bisphenol A the preferred wavelength (F2) range is 5908 to 55997 $cm^{-1}$. The wavelength for the base depends upon the specific base being monitored, for instance for caustic the preferred wavelength (F3) range for hydroxide is 5642 to 5723 $cm^{-1}$. The wavelength (F4) range for the temperature compensation is 5457 to 5533 $cm^{-1}$.

To illustrate the practice of the present invention, examples of preferred embodiments are set forth below. However, these examples do not in any manner restrict the scope of this invention.

EXAMPLES

A Process Photometer PIR3502 available from ABB Inc. is installed in a commercial scale interfacial polycarbonate manufacturing process for manufacturing bisphenol A polycarbonate. Examples 1 to 4 are linear polycarbonate polymers having melt flow rates of 3 g/10 min determined at 300° C. and a load of 1.2 kilograms, 14 g/10 min, 23 g/10 min, and 80 g/10 min, respectively. The aqueous bisphenolate mixture is reacted with a carbonate precursor, preferably phosgene, in the polymerization reactor to produce oligomers that are then coupled to the desired polymer molecular weight. The phases are separated, washed, and the polycarbonate isolated. The chain terminator used is tertiary-butyl phenol and the coupling catalyst is triethyl amine. The chain terminator concentration is held constant during the reaction. The appropriate concentrations of the reactants and reaction conditions are easily determined by one skilled in the art.

The sample line for the aqueous bisphenolate A mixture sample loops on/off the main process line between the solution tank and the polymerization reactor. The sample line and the sample are heated to about 60° C. (the sample is heated in a sample handling system prior to NIR analysis). The Process Photometer PIR3502 takes reading at four wavelengths: (1) 7633 to 7752 $cm^{-1}$ (reference), (2) 5908 to 55997 $cm^{-1}$ (bisphenolate), (3) 5642 to 5723 $cm^{-1}$ (hydroxide), and 5457 to 5533 $cm^{-1}$ (temperature compensation). The output from the Process Photometer PIR3502 is fed into the process computer control for real time adjustments to the feed rate of the bisphenolate A solution into the polymerization reactor.

Comparative Examples A to D are polycarbonate polymers made by the exact same manner as Examples 1 to 4 with the exception that the bisphenol A feed rate is controlled manually based on analysis of aqueous bisphenate mixture samples taken by grab samples and analyzed off line in a lab every three hours.

The results for Examples 1 to 4 and Comparative Examples A to B are summarized in Table 1 and are reported as the amount a material produced which is out of product specification. Product specifications are set for upper and lower acceptable polycarbonate molecular weight for a corresponding MFR. Molecular weights are weight average molecular weights. Results are given as percent (%) out of specification. In Table 1, MFR is determined according to ASTM D 1238 on a Zwick Plastometer 4105 melt flow rate apparatus at conditions of 300° C. and an applied load of 1.2 kg.

TABLE 1

| Example/Comparative Example | MFR, g/10 min | % Out Of Specification ||
| | | w/o Online Analysis | w Online Analysis |
| --- | --- | --- | --- |
| 1/A | 3 | 2.9 | 0 |
| 2/B | 14 | 4.0 | 3.7 |
| 3/C | 23 | 5.5 | 4.6 |
| 4/D | 80 | 18.9 | 4.2 |

The invention claimed is:

1. A method for controlling a dihydric phenol to chain terminator ratio in an interfacial polycarbonate polymerization process by measuring the concentration of dihydric phenolate, hydroxide, or both in an aqueous dihydric phenolate solution prior to reacting said solution with a carbonate precursor and chain terminator to produce a polycarbonate polymer, comprising the steps of:

i setting a target range for the dihydric phenol to chain terminator ratio;
 ii introducing dihydric phenol and base at specific and independent feed rates into said solution;
 iii setting target concentration ranges for dihydric phenolate and/or hydroxide in said solution;
 iv introducing said solution, the carbonate precursor, and the chain terminator into a polymerization reactor at specific and independent feed rates;
 v analyzing said solution, online prior to entering the polymerization reactor by vibrational spectroscopy measuring the absorbance or scattering intensity of at least one wavelength as a reference wherein said solution has little to no absorbance, at least one wavelength wherein the dihydric phenolate absorbs, at least one wavelength wherein hydroxide absorbs, and at least one wavelength for temperature compensation;
 vi calculating the concentration of the dihydric phenolate and/or hydroxide in said solution based on the vibrational spectrometer analysis;
 vii comparing the calculated concentrations to the target concentration ranges; and
 viii using process control, when necessary, to adjust the feed rates of one or more of the dihydric phenol, the base, the chain terminator, and/or the dihydric phenolate solution to maintain the dihydric phenolate to chain terminator target range.

2. The method of claim 1 wherein the feed rate for the dihydric phenol and the feed rate for the base are kept constant and (1) the feed rate of the dihydric phenolate solution is held constant and the feed rate for the chain terminator is controlled, (2) the feed rate for the chain terminator is held constant and the feed rate for the dihydric phenolate solution is controlled, or (3) both the feed rates of the dihydric phenolate solution and the chain terminator are controlled to maintain the dihydric phenolate to chain terminator target range.

3. The method of claim 1 wherein the dihydric phenol is bisphenol A; the source for hydroxide is caustic; the carbonate precursor is phosgene; the chain terminator is phenol, para-cumyl phenol, or para-tertiary-butylphenol; and the polycarbonate polymer is a bisphenol A polycarbonate polymer.

4. The method of claim 3 wherein the bisphenol A polycarbonate polymer is linear.

5. The method of claim 3 further comprising a branching agent and the polycarbonate polymer is a branched bisphenol A polycarbonate polymer.

6. The method of claim 1 wherein the polycarbonate polymer has a melt flow rate as determined at 300° C. and a load of 1.2 kilograms of from about 1 to about 100 grams per 10 minutes.

7. The method of claim 1 wherein the online vibrational spectroscopic analysis is performed by a Raman spectrometer, a mid infrared spectrometer, or a near infrared spectrometer.

8. The method of claim 7 wherein the online vibrational spectroscopic analysis is a near infrared analysis preformed by a single transmission cell, single light source, multi-filter photometer capable of measuring absorbance continuously and alternatively from 2 up to and including 8 different wavelengths.

9. The method of claim 1 wherein the reference wavelength range is 7633 to 7752 $cm^{-1}$, the dihydric phenolate wavelength range is 5908 to 5997 $cm^{-1}$, the hydroxide wavelength range is 5642 to 5723 $cm^{-1}$, and the temperature compensation wavelength range 5457 to 5533 $cm^{-1}$.

10. The method of claim 1 further comprising the step of maintaining the temperature of the dihydric phenolate solution during the analysis within a temperature range of about 55° C. to 65° C.

* * * * *

UNITED STATES PATENT AND TRADEMARK OFFICE
CERTIFICATE OF CORRECTION

PATENT NO.       : 8,426,531 B2                                               Page 1 of 1
APPLICATION NO. : 13/254062
DATED            : April 23, 2013
INVENTOR(S)      : Chauvel, Jr. et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 39 days.

Signed and Sealed this
Eighth Day of September, 2015

Michelle K. Lee
*Director of the United States Patent and Trademark Office*